(12) United States Patent
Cafiero et al.

(10) Patent No.: US 10,959,944 B2
(45) Date of Patent: *Mar. 30, 2021

(54) PROCESS FOR PREPARING A DRY POWDER FORMULATION COMPRISING AN ANTICHOLINERGIC, A CORTICOSTEROID AND A BETA-ADRENERGIC

(71) Applicant: CHIESI FARMACEUTICI S.P.A., Parma (IT)

(72) Inventors: Claudio Cafiero, Parma (IT); Leonardo Ortenzi, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/986,796

(22) Filed: Aug. 6, 2020

(65) Prior Publication Data

US 2020/0360278 A1 Nov. 19, 2020

Related U.S. Application Data

(63) Continuation of application No. 16/113,051, filed on Aug. 27, 2018, now Pat. No. 10,786,451, which is a continuation of application No. 15/351,510, filed on Nov. 15, 2016, now Pat. No. 10,086,003.

(30) Foreign Application Priority Data

Nov. 16, 2015 (EP) ..................... 15194661

(51) Int. Cl.
| | | |
|---|---|---|
| *A61K 9/00* | (2006.01) | |
| *A61K 45/06* | (2006.01) | |
| *A61K 31/194* | (2006.01) | |
| *A61K 31/573* | (2006.01) | |
| *A61K 47/12* | (2006.01) | |
| *A61K 47/26* | (2006.01) | |
| *A61K 9/14* | (2006.01) | |
| *A61K 9/16* | (2006.01) | |
| *A61K 31/167* | (2006.01) | |
| *A61K 31/40* | (2006.01) | |
| *A61K 31/57* | (2006.01) | |
| *A61K 31/00* | (2006.01) | |
| *A61P 43/00* | (2006.01) | |
| *A61P 29/00* | (2006.01) | |
| *A61P 11/08* | (2006.01) | |
| *A61P 11/06* | (2006.01) | |
| *A61P 11/00* | (2006.01) | |

(52) U.S. Cl.
CPC ............ *A61K 9/0075* (2013.01); *A61K 9/145* (2013.01); *A61K 9/1617* (2013.01); *A61K 9/1623* (2013.01); *A61K 31/00* (2013.01); *A61K 31/167* (2013.01); *A61K 31/194* (2013.01); *A61K 31/40* (2013.01); *A61K 31/57* (2013.01); *A61K 31/573* (2013.01); *A61K 45/06* (2013.01); *A61K 47/12* (2013.01); *A61K 47/26* (2013.01)

(58) Field of Classification Search
CPC .... A61K 9/0075; A61K 45/06; A61K 31/194; A61K 31/573; A61K 47/12; A61K 47/26; A61K 9/145; A61K 9/1617; A61K 9/1623; A61K 31/167; A61K 31/40; A61K 31/57; A61K 31/00; A61P 29/00; A61P 11/08; A61P 11/06; A61P 11/00
See application file for complete search history.

(56) References Cited

U.S. PATENT DOCUMENTS

2003/0180227 A1   9/2003   Staniforth et al.

FOREIGN PATENT DOCUMENTS

WO   2015/004243 A1   1/2015

OTHER PUBLICATIONS

European Search Report dated Apr. 14, 2016 issued in corresponding application No. 15194661.3.

*Primary Examiner* — Trevor Love
(74) *Attorney, Agent, or Firm* — Oblon, McClelland, Maier & Neustadt, L.L.P.

(57) ABSTRACT

Dry powder formulations for inhalation comprising a combination of an anti-cholinergic, a long-acting beta$_2$-adrenoceptor agonist, and, optionally, an inhaled corticosteroid are useful for the prevention and/or treatment of an inflammatory and/or obstructive airways disease.

16 Claims, No Drawings

PROCESS FOR PREPARING A DRY POWDER FORMULATION COMPRISING AN ANTICHOLINERGIC, A CORTICOSTEROID AND A BETA-ADRENERGIC

CROSS REFERENCES TO RELATED APPLICATIONS

This application is a continuation of U.S. application Ser. No. 15/351,510, filed on Nov. 15, 2016, and claims priority to European Patent Application No. 15194661.3, filed on Nov. 16, 2015, which is incorporated herein by reference in its entirety.

BACKGROUND OF THE INVENTION

Field of the Invention

The present invention relates to powder formulations for administration by inhalation by means of a dry powder inhaler. In particular, the present invention relates to processes for preparing a dry powder formulation comprising a combination of an anticholinergic, a $beta_2$-adrenoceptor agonist, and, optionally an inhaled corticosteroid.

Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung disease include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aim of COPD management includes not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing, and in particular, combination therapies, with a view to their complementary modes of action enabling multiple components of the disease to be addressed. Evidence from recent clinical trials indicates that triple therapy, combining an anticholinergic with an inhaled corticosteroid, and a long-acting $\beta_2$-adrenoceptor agonist, may provide clinical benefits additional to those associated with each treatment alone in patients with more severe COPD.

Currently, there are several recommended classes of therapy for COPD, of which bronchodilators such as $\beta_2$-agonists and anti-cholinergics are the mainstay of symptom management in mild and moderate diseases, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicates that triple therapy, combining an anticholinergic with a long-acting N-agonist (LABA), and an ICS, may provide clinical benefits additional to those associated with each treatment alone in patients with moderate to severe forms of respiratory diseases, particular moderate to severe COPD.

An interesting triple combination, presently under investigation, includes:

i) formoterol, particularly its fumarate salt (hereinafter indicated as FF), a long acting beta-2 adrenergic receptor agonist, currently used clinically in the treatment of asthma, COPD and related disorders;

ii) glycopyrronium bromide, an anticholinergic recently approved for the maintenance treatment of COPD; and iii) beclometasone dipropionate (BDP) a potent anti-inflammatory corticosteroid, available under a wide number of brands for the prophylaxis and/or treatment of asthma and other respiratory disorders.

Powder formulations for inhalation by Dry Powder Inhalers (DPIs) containing all said three active ingredients in a fixed combination are disclosed in WO 2015/004243, which is incorporated herein by reference in its entirety. Said formulation takes advantage of the technology platform disclosed in WO 01/78693, which is incorporated herein by reference in its entirety, entailing the use of carrier constituted of a fraction of coarse excipient particles and a fraction made of fine excipient particles and magnesium stearate.

However, the teaching of WO 2015/004243, which is incorporated herein by reference in its entirety, is mainly focused at providing a powder formulation wherein all the active ingredients have very small particle size in order to reach the distal tract of the respiratory tree.

On the other hand, for the treatment of some forms of respiratory diseases COPD, to maximize bronchodilatation, it would be advantageous to provide a powder formulation wherein the anticholinergic drug may also significantly achieve the upper tract of the respiratory tract to favor their bronchodilator activity, while allowing the inhaled corticosteroid and the LABA mainly reaching the bronchiolo-alveolar distal part. The problem is solved by the formulation of the present invention and process for its preparation thereof.

SUMMARY OF THE INVENTION

Accordingly, it is one object of the present invention to provide novel powder formulations.

It is another object of the present invention to provide novel powder formulations wherein the anticholinergic drug may also significantly achieve the upper tract of the respiratory tract to favor their bronchodilator activity, while allowing the inhaled corticosteroid and the LABA mainly reaching the bronchiolo-alveolar distal part.

It is another object of the present invention to provide novel methods of preventing/treating a disease of the respiratory tract by administering such a formulation.

These and other objects, which will become apparent during the following detailed description, have been achieved by the inventors' discovery of a process for preparing a powder formulation for inhalation for use in a dry powder inhaler, said powder formulation comprising:

(A) a carrier, comprising:

(a) a fraction of coarse particles of a physiologically acceptable carrier having a mean particle size of at least 175 µm; and (b) a fraction of fine particles, consisting of a mixture of 90 to 99.5 percent by weight of particles of a physiologically acceptable excipient and 0.5 to 10 percent by weight of a salt of a fatty acid, wherein at least 90% of all said fine particles have a volume diameter lower than 15 microns, wherein the weight ratio of said fine particles to said coarse particles 5:95 to 30:70; and (B) micronized particles of an antimuscarinic drug, a long-acting pragonist, and, optionally, an inhaled corticosteroid, as active ingredients, wherein said process comprises:

(i) mixing said carrier, said long-acting $\beta_2$-agonist, and, optionally, said inhaled corticosteroid in a vessel of a shaker mixer at a speed of rotation not lower than 16 r.p.m. for a time of not less than 60 minutes, to obtain a first mixture; and (ii) adding said anti-muscarinic drug to said first mixture, to obtain a second mixture, and mixing said second mixture at a speed of rotation not higher than 16 r.p.m. for a time of not more than 40 minutes.

In a preferred embodiment, the anti-muscarinic drug is glycopyrronium bromide, the inhaled corticosteroid (ICS) is beclometasone dipropionate, the long-acting $\beta_2$-agonist (LABA) is formoterol fumarate dihydrate, and the salt of fatty acid is magnesium stearate.

Therefore, in a second aspect, the present invention is directed to a powder formulation for use in any dry powder inhaler comprising:

(A) a carrier, comprising:

(a) a fraction of coarse particles of a physiologically acceptable carrier having a mean particle size of at least 175 µm; and (b) a fraction of fine particles consisting of a mixture of 90 to 99.5 percent by weight of particles of a physiologically acceptable excipient and 0.5 to 10 percent by weight of magnesium stearate, wherein at least 90% of all said fine particles have a volume diameter lower than 15 microns, wherein the weight ratio of said fine particles to said coarse particles is 5:95 to 30:70; and (B) micronized particles of glycopyrronium bromide, formoterol fumarate dihydrate, and, optionally, beclometasone dipropionate, as active ingredients, wherein said formulation is obtainable by a process comprising:

(i) mixing said carrier, said formoterol fumarate dihydrate, and, optionally, said beclometasone dipropionate in a vessel of a shaker mixer at a speed of rotation not lower than 16 r.p.m. for a time of not less than 60 minutes, to obtain a first mixture; and (ii) adding said glycopyrronium bromide to said first mixture, to obtain a second mixture, and mixing said second mixture at a speed of rotation not higher than 16 r.p.m. for a time of not more than 40 minutes; and whereby the mid fine particle fraction of glycopyrronium bromide is higher than 25%, preferably between 28 and 40%.

In a third aspect, the invention provides a dry powder inhaler device filled with the above dry powder formulations.

In a fourth aspect, the present invention refers to the claimed formulations for use in the prevention and/or treatment of an inflammatory and/or obstructive airways disease, in particular asthma or chronic obstructive pulmonary disease (COPD).

In a fifth aspect, the present invention provides a method for the prevention and/or treatment of an inflammatory and/or obstructive airways disease, in particular asthma or chronic obstructive pulmonary disease (COPD), comprising administering by inhalation, to a subject in need thereof, an effective amount of the formulations of the invention.

In a sixth aspect, the present invention refers to the use of the claimed formulations in the manufacture of a medicament for the prevention and/or treatment of an inflammatory and/or obstructive airways disease, in particular asthma or chronic obstructive pulmonary disease (COPD).

DETAILED DESCRIPTION OF THE PREFERRED EMBODIMENTS

The terms "muscarinic receptor antagonists", "antimuscarinic drugs" and "anticholinergic drugs" can be used synonymously.

The term "pharmaceutically acceptable salt of glycopyrrolate" refers to a salt of the compound (3S,2'R), (3R,2'S)-3-[(cyclopentylhydroxyphenylacetyl)oxy]-1,1-dimethylpyrrolidinium in approximately 1:1 racemic mixture, also known as glycopyrronium salt.

The term "pharmaceutically acceptable salt of formoterol" refers to a salt of the compound 2'-hydroxy-5'-[(RS)-1-hydroxy-2 {[(RS)-p-methoxy-α-methylphenethyl]amino}ethyl]formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy) acetyl]-6,7,8,9,10,11,12,13,14,15,16,17-dodecahydro-3H-cyclopenta[α]phenanthren-17-yl propionate.

The term "pharmaceutically acceptable salt" comprises inorganic and organic salts. Examples of organic salts may include formate, acetate, trifluoroacetate, propionate, butyrate, lactate, citrate, tartrate, malate, maleate, succinate, methanesulfonate, benzenesulfonate, xinafoate, pamoate, and benzoate. Examples of inorganic salts may include fluoride chloride, bromide, iodide, phosphate, nitrate and sulfate.

The term "physiologically acceptable excipient" refers to a pharmacologically-inert substance to be used as a carrier. In the context of the present invention, salts of fatty acids, that are also physiologically acceptable excipients are considered as additives.

The expression "shaker mixer" refers to a versatile mixer having a wide and adjustable range of speed of rotation and inversion cycles. In said mixers, the mixing container is gimbal-mounted. Two rotation axes are positioned perpendicularly each other, and are powered independently. The turning direction and rotational speed of both axes is subject to continual and independent change. The setting of these kind of mixing process parameters is able to guarantee an high value of mixing efficiency. A typical shaker mixer is commercially available as dyna-MIX™ (Willy A. Bachofen AG, Switzerland) or 3D.S mixer (Erhard Muhr GmbH, Germany).

The expression "tumbler mixer" refers to a mixer that works with different mixing times and mixing speeds but with a typical movement characterized by the interaction of rotation, translation and inversion.

A typical tumbler mixer is commercially available as Turbula™ (Willy A. Bachofen AG, Switzerland).

The expression instant or high-shear mixer refers to mixers wherein a rotor or impeller, together with a stationary component known as a stator is used either in a tank containing the powder to be mixed to create a shear.

Typical high-shear mixers are P 100 and P 300 (Diosna GmbH, Germany), Roto Mix (IMA, Italy), and Cyclomix™ (Hosokawa Micron Group Ltd, Japan).

The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90 of the particles, respectively.

Another common approach to define the particle size distribution is to cite three values: i) the median diameter d(0.5) which is the diameter where 50% of the distribution is above and 5% is below; ii) d(0.9), where 90% of the distribution is below this value; and iii) d(0.1), where 10% of the distribution is below this value.

The span is the width of the distribution based on the 10%, 50% and 90% quantile and is calculated according to the formula.

$$\text{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation the particle size of the active ingredients can be determined by scanning electron microscopy according to methods known to the skilled person in the art.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able of ensuring an accurate and reproducible delivery of the therapeutically effective dose.

Flow characteristics can be evaluated by different tests such as angle of repose, Carr's index, Hausner ratio or flow rate through an orifice.

In the context of the present application the flow properties were tested by measuring the flow rate through an orifice according to the method described in the European Pharmacopeia (Eur. Ph.) 8.6, 8$^{th}$ Edition, which is incorporated herein by reference in its entirety. The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI) or Next Generation Impactor (NGI), according to procedures reported in common Pharmacopoeias, in particular in the European Pharmacopeia (Eur. Ph.) 8.4, 8$^{th}$ Edition, which is incorporated herein by reference in its entirety.

It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 micron.

In the context of the invention, the formulation is defined as extrafine formulation when, upon inhalation, the active ingredients are delivered with a fraction of particles having a particle size equal to or lower than 2.0 micron equal to or higher than 20%, preferably equal to or higher than 25%, more preferably equal to or higher than 30% a and/or it is able of delivering a fraction of particles having a particle size equal to or lower than 1.0 micron equal to or higher than 10%.

With the term "mid FPF" is defined as the fraction of delivered dose having a particle size comprised between 2.0 and 5.0. A mid FPF higher than 25% is an index of a good deposition in the proximal part of the lungs.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al. J. Pharm. Pharmacol. 34,700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "chemically stable" refers to a formulation that, upon storage, meets the requirements of the EMEA Guideline CPMP/QWP/122/02, which is incorporated herein by reference in its entirety, referring to 'Stability Testing of Existing Active Substances and Related Finished Products'.

The term "surface coating" refers to the covering of the surface of the carrier particles by forming a film of magnesium stearate around said particles. The thickness of the film has been estimated by X-ray photoelectron spectroscopy (XPS) to be approximately of less than 10 nm. The percentage of surface coating indicates the extent by which magnesium stearate coats the surface of all the carrier particles.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i. e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GNA), which is incorporated to herein by reference in its entirety, "uncontrolled persistent asthma" is defined as a form characterized by daily symptoms, frequent exacerbations, frequent nocturnal asthma symptoms, limitation of physical activities, forced expiratory volume in one second ($FEV_1$) equal to or less than 80% predicted and with a variability higher than 30%. According to the Global Initiative for Asthma (GINA) guidelines 2014, which is incorporated herein by reference in its entirety, "partially uncontrolled asthma" is defined as a form characterized by less than twice a week daily symptoms, less than twice a month, nocturnal asthma symptoms, and a forced expiratory volume in one second ($FEV_1$) higher than 80% with a variability comprised between 20 and 30%.

According to the Global initiative for chronic Obstructive Pulmonary Disease (GOLD) guidelines, which is incorporated herein by reference in its entirety, "severe COPD" is a form characterized by a ratio between $FEV_1$ and the Forced Vital Capacity (FVC) lower than 0.7 and $FEV_1$ between 30% and 50% predicted. The very severe form is further characterized by chronic respiratory failure.

"Therapeutically effective dose" means the quantity of active ingredients administered at one time by inhalation upon actuation of the inhaler. Said dose may be delivered in one or more actuations, preferably one actuation (shot) of the inhaler. The term "actuation" refers to the release of active ingredients from the device by a single activation (e.g. mechanical or breath).

Wherein a numerical range is stated herein, the endpoints are included.

The present invention is directed to a process for the preparation of a dry powder formulation for use in a dry powder inhaler (DPI) comprising a carrier, and micronized particles of an anticholinergic, an inhaled corticosteroid (ICS), and a long-acting $\beta_2$-agonist (LABA) as active ingredients.

The LABA active ingredient, that may be present in form of pharmaceutically acceptable salts and/or solvate form thereof, can be selected from a group, which include, but it is not limited to, formoterol, salmeterol, indacaterol, olodaterol, vilanterol and the ultra-long-acting β2-adrenoreceptor agonist (uLABA) compound quoted with the code AZD3199.

The anticholinergic, that is usually present in form of pharmaceutically acceptable inorganic salts, can be selected from a group which include, but it is not limited to, glycopyrronium bromide or chloride, tiotropium bromide, umeclidinium bromide, aclidinium bromide, and the compound quoted with the code GSK 233705.

The ICS, that may be anhydrous or present in form of hydrates, may be selected from a group which includes, but it is not limited to, beclometasone dipropionate and its monohydrate form, budesonide, fluticasone propionate, fluticasone furoate, and mometasone furoate.

Preferably, the LABA is formoterol fumarate dihydrate, the ICS is beclometasone dipropionate, and the anticholinergic is glycopyrronium bromide.

The carrier A) comprises a fraction of fraction of coarse excipient particles a) and a fraction of fine particles b).

The coarse excipient particles of the fraction a) must have a mass median diameter equal to or higher 175 micron.

Advantageously, all the coarse particles have a mass diameter in the range of 100 to 600 micron.

In certain embodiments of the invention, the mass diameter of said coarse particles might be from 150 to 500 micron, preferably from 200 to 400 micron.

In a preferred embodiment of the invention, the mass diameter of the coarse particles is from 210 to 360 micron.

In general, the skilled person shall select the most appropriate size of the coarse excipient particles if commercially available or by sieving, using a proper classifier.

Advantageously, the coarse excipient particles may have a relatively highly fissured surface, that is, on which there are clefts and valleys and other recessed regions, referred to herein collectively as fissures. The "relatively highly fissured" coarse particles can be defined in terms of fissure index and/or rugosity coefficient as described in WO 01/78695 and WO 01/78693, which are incorporated herein by reference in their entireties, and they could be characterized according to the description therein reported. Advantageously, the fissure index of said coarse particles is of at least 1.25, preferably of at least 1.5, more preferably of at least 2.0, Said coarse particles may also be characterized in terms of tapped density or total intrusion volume measured as reported in WO 01/78695, which is incorporated herein by reference in its entirety.

The tapped density of said coarse particles could advantageously be less than 0.8 $g/cm^3$, preferably from 0.8 to 0.5 $g/cm^3$. The total intrusion volume could be of at least 0.8 $cm^3$, preferably at least 0.9 $cm^3$.

The fraction of fine particles b), in turn, consists of 90 to 99.5 percent by weight of particles of a physiologically acceptable excipient and 0.5 to 10 percent by weight of magnesium stearate wherein at least 90% of said particles have a volume diameter lower than 15 micron, preferably lower than 12 micron.

In one of the embodiment of the present invention, said fraction b) may be obtained by subjecting the excipient particles and the magnesium stearate particles to co-micronization by milling, advantageously in a ball mill.

In some cases, co-micronization for at least two hours may be found advantageous, although it will be appreciated that the time of treatment will generally be such that a desired size reduction is obtained. In a more preferred embodiment of the invention the particles are co-micronized by using a jet mill.

In another embodiment of the present invention, at least 90% of the particles of fraction b) have a volume diameter lower than 15 micron, preferably lower than 12 micron, as well as the volume median diameter of said particles is from 3 to 7 micron, preferably from 4 to 6 micron and no more than 10% of said particles have a diameter lower than 2.5 micron, preferably lower than 2.0 micron.

In order to achieve the control of the above particle size which allow improving the flowability of the powder, a mixture of micronized excipient particles with, optionally micronized, magnesium stearate particles is subjected to co-mixing in any suitable mixer preferably for at least one hour, more preferably for at least two hours or in a high-energy mixer for more than 30 minutes, preferably for at least one hour, more preferably for at least two hours; otherwise the components are subjected to co-mixing in a high-energy apparatus for a period of less than about 30 minutes, preferably less than 20 minutes as disclosed in the co-pending application WO 2015/004243 which is incorporated herein by reference in its entirety.

Since the co-mixing step does not alter the particle size of the fraction of said particles, the person skilled in the art shall select the suitable size of the fine particles of the physiologically acceptable excipient as well as of the salt of the fatty acid, either by sieving, by using a classifier to achieve the desired particle size distribution.

Materials of the desired particle size distribution are also commercially available.

It has been found that the technology platform disclosed in WO 01/78693, which is incorporated herein by reference in its entirety, might be suitable for preparing a dry powder formulation comprising three different active ingredients at different therapeutically effective dosages.

Advantageously, the fine and coarse excipient particles may consist of any pharmacologically inert, physiologically acceptable material or combination thereof; preferred excipients are those made of crystalline sugars, in particular lactose; the most preferred are those made of α-lactose monohydrate.

Preferably, the coarse excipient particles and the fine excipient particles both consist of α-lactose monohydrate.

Advantageously, the salt of the fatty acid, which acts as an additive to improve the respirable fraction, consists of a salt of fatty acids such as lauric acid, palmitic acid, stearic acid, behenic acid, or derivatives (such as esters and salts) thereof. Specific examples of such materials are: magnesium stearate; sodium stearyl fumarate; sodium stearyl lactylate; sodium lauryl sulfate, and magnesium lauryl sulfate.

The preferred salt of fatty acid is magnesium stearate.

Advantageously, when it is used as the additive, magnesium stearate coats the surface of the excipient particles of fine fraction b) in such a way that the extent of the surface coating is at least of 10%, more advantageously, higher than 20%.

In some embodiments, depending on the amount of magnesium stearate as well as on the processing conditions, an extent of the surface coating higher than 50%, preferably higher than 60% could be achieved.

The extent to which the magnesium stearate coats the surface of the excipient particles may be determined by X-ray photoelectron spectroscopy (XPS), a well-known tool for determining the extent as well as the uniformity of distribution of certain elements on the surface of other substances. In the XPS instrument, photons of a specific energy are used to excite the electronic states of atoms below the surface of the sample. Electrons ejected from the surface are energy filtered via a hemispherical analyser (HSA) before the intensity for a defined energy is recorded by a detector. Since core level electrons in solid-state atoms are quantized, the resulting energy spectra exhibit resonance peaks characteristic of the electronic structure for atoms at the sample surface.

Typically XPS measurements are taken on an Axis-Ultra instrument available from Kratos Analytical (Manchester, UK) using monochromated Al Kα radiation (1486.6 eV) operated at 15 mA emission current and 10 kV anode potential (150 W). A low energy electron flood gun is used to compensate for insulator charging. Survey scans, from which quantification of the detected elements are obtained, are acquired with analyser pass energy of 160 eV and a 1 eV step size. High-resolution scans of the C 1s, O 1s, Mg 2s, N 1s and Cl 2p regions are acquired with pass energy of 40 eV and a 0.1 eV step size. The area examined is approximately 700 μm×300 μm for the survey scans and a 110 μm diameter spot for the high-resolution scans.

In the context of the present invention, it is possible to calculate by XPS both the extent of coating and the depth of the magnesium sterate film around the lactose particles. The extent of magnesium stearate (MgSt) coating is estimated using the following equation:

$$\% \text{ MgSt coating} = (\% \text{ Mg}_{sample}/\% \text{ Mg}_{ref}) \times 100$$

where:

$\text{Mg}_{sample}$ is the amount of Mg in the analyzed mixture; and $\text{Mg}_{ref}$ is the amount of Mg in the reference sample of commercially available MgSt.

Usually the values are calculated as a mean of two different measurements. Typically, an accuracy of 10% is quoted for routinely performed XPS experiments.

Alternatively, when the excipient particles are made of lactose, preferably of alpha-lactose monohydrate, the extent of surface coating may be determined by water contact angle measurement, and then by applying the equation known in the literature as Cassie and Baxter, for example cited at page 338 of Colombo I et al *Il Farmaco* 1984, 39(10), 328-341, which is incorporated herein by reference in its entirety, and reported to below.

$$\cos \vartheta_{mixture} = f_{MgSt} \cos \vartheta_{MgSt} + f_{lactose} \cos \vartheta_{lactose}$$

where:

$f_{MgSt}$ and $f_{lactose}$ are the surface area fractions of magnesium stearate and of lactose;

$\vartheta_{MgSt}$ is the water contact angle of magnesium stearate;

$\vartheta_{lactose}$ is the water contact angle of lactose; and $\vartheta_{mixture}$ are the experimental contact angle values.

For the purpose of the present invention, the contact angle may be determined with methods that are essentially based on a goniometric measurement. These imply the direct observation of the angle formed between the solid substrate and the liquid under testing. It is therefore quite simple to carry out, being the only limitation related to possible bias stemming from intra-operator variability. It should be however underlined that this drawback can be overcome by adoption of a fully automated procedure, such as a computer assisted image analysis. A particularly useful approach is the sessile or static drop method which is typically carried out by depositing a liquid drop onto the surface of the powder in form of disc obtained by compaction (compressed powder disc method).

Within the limits of the experimental error, a good consistency has been found between the values of extent of coating as determined by XPS measurements, and those as estimated by the theoretical calculations based on the Cassie and Baxter equation.

The extent to which the magnesium stearate coats the surface of the excipient particles may also be determined by scanning electron microscopy (SEM), a well-known versatile analytical technique.

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of the excipient particles.

SEM may alternatively be combined with IR or Raman spectroscopy for determining the extent of coating, according to known procedures.

The step of mixing the coarse excipient particles a) with the fraction of fine particles b) is typically carried out in any suitable mixer, e.g. tumbler mixers such as Turbular™, or high shear mixers such as those available from Diosna, for at least 5 minutes, preferably for at least 30 minutes, more preferably for at least two hours.

In a general way, the skilled person shall adjust the time of mixing and the speed of rotation of the mixer to obtain a homogenous mixture.

When spheronized coarse excipient particles are desired to obtain hard-pellets according to the definition reported above, the step of mixing shall be typically carried out for at least four hours.

In one embodiment, the carrier consisting of the fraction of coarse particles a) and the fraction of fine particles b) may be prepared by mixing any suitable mixer. For instance, if a Turbula™ mixer is utilized, the two fractions shall be mixed at a rotation speed of 11 to 45 rpm, preferably 16 to 32 rpm for a period of at least 30 minutes, preferably comprised between 30 and 300 minutes, more preferably between 150 and 240 minutes.

Optionally, before it is mixed with the fraction of coarse particles a), the fraction of fine particles b) may be subjected to a conditioning step according to the conditions disclosed in WO 2011/131663, which is incorporate herein by reference in its entirety.

In a particular embodiment, the carrier may be obtained by co-mixing the coarse excipient particles, the micronized excipient particles and micronized magnesium stearate particles together in any suitable mixer. For instance, if the Turbula™ mixer is utilized, the three components shall be mixed for a time higher than 30 minutes, advantageously comprised between 60 and 300 minutes.

The ratio between the fraction of line particles b) and the fraction of coarse particles a) shall from 1:99 to 30:70% by weight, preferably from 2:98 to 20:80% by weight.

Preferably, the ratio may be from 5:95 to 15:85% by weight.

In certain embodiments, the ratio may be 10:90 by weight, while in other embodiments, the ratio may be 5:95 by weight.

Advantageously, in the carrier, when it is present, magnesium stearate coats the surface of the fine and/or coarse excipient particles in such a way that the extent of the surface coating is at least of 5%, more advantageously, higher than 10%, preferably equal to or higher than 15%.

The extent to which the magnesium stearate coats the surface of the excipient particles may be determined as reported above.

In step i), the carrier, the LABA active ingredient, and, optionally the ICS active ingredient, are loaded in the vessel of a suitable shaker mixer having a wide and adjustable range of speed of rotation and inversion cycles.

It has indeed been found that said type of mixers is particularly suitable due to their versatility. In fact, with said mixers, frequent changes in the revolution cycles can be set in order to continuously change the powder flow inside the mixing drum and create different powder flow patterns to increase mixing efficacy.

The carrier is mixed in a shaker mixer with the ICS and the LABA active ingredients at a speed of rotation not lower than 16 r.p.m. preferably from 16 to 32 r.p.m., for a time of not less than 60 minutes, preferably from 60 to 120 minutes.

In step ii), the anti-muscarinic drug is added to the above blend and mixed at a speed of rotation not higher than 16 r.p.m., preferably 15 r.p.m. or lower, for a time of not more than 40 minutes, preferably between 20 and 40 minutes.

In a preferred embodiment of the invention, the dynaMIX™ mixer is utilized.

Optionally, the resulting mixture is sieved through a sieve. The skilled person shall select the mesh size of the sieve depending on the particle size of the coarse particles.

The blend of step ii) is finally mixed in any suitable mixer to achieve a homogeneous distribution of the active ingredients.

The skilled person shall select the suitable mixer and adjust the time of mixing and the speed of rotation of the mixer to obtain a homogenous mixture.

Advantageously, each active ingredient is present in the formulation of the invention in a crystalline form, more preferably with a crystallinity degree higher than 95%, even more preferably higher than 98%, as determined according to known methods.

Since the powder formulation obtained with the process of the invention should be administered to the lungs by inhalation, at least 99% of said particles [d(v,0.99)] shall have a volume diameter equal to or lower than 10 micron, and substantially all the particles have a volume diameter comprised between 8 and 0.4 micron.

Advantageously, in order to better achieve the distal tract of the respiratory tree, 90% of the micronized particles of the ICS and LABA active ingredients shall have a volume diameter lower than 6.0 micron, preferably equal to or lower than 5.0 micron, the volume median diameter shall be from 1.2 to 2.5 micron, preferably from 1.3 to 2.2 micron, and no more than 10% of said shall have a diameter lower than 0.6 micron, preferably equal to or lower than 0.7 micron, more preferably equal to or lower than 0.8 micron It follows that the width of the particle size distribution of the particles of the ISC and LABA active ingredients, expressed as a span, shall be advantageously comprised between 1.0 and 4.0, more advantageously between 1.2 and 3.5 According the Chew et al J Pharm Pharmaceut Sci 2002, 5, 162-168, which is incorporated herein by reference in its entirety, the span corresponds to $[d(v, 0.9)-d(v,0.1)]/d(v, 0.5)$.

In the case of the anticholinergic drug, in order to achieve both the distal and upper tract of the respiratory tree, 90% of the micronized particles shall have a volume diameter equal to or lower than 8.0 micron, preferably equal to or lower than 7 micron, the volume median diameter shall be from 1.2 to 4.0 micron, preferably from 1.7 to 3.5 micron, and no more than 10% of said have a diameter lower than 0.5 micron, preferably equal to or lower than 0.6 micron, more preferably equal to or lower than 0.8 micron.

It follows that the width of the particle size distribution of the particles of the anticholinergic drug, expressed as a span, shall be advantageously comprised between 1.0 and 5.0, more advantageously between 1.2 and 4.0.

The size of the particles active is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

In a preferred embodiment, the Helos Aspiros instrument (Sympatec GmbH, Clausthal-Zellerfeld, Germany) is utilized. Typical conditions are: Fraunhofer FREE or Fraunhofer HRLD algorithm, R1 (0.1/0.18-35 micron) or R2 (0.25/0.45-87.5 micron) lens, 1 bar pressure.

As for the particle size determination, a CV of ±30% for the d(v0,1) and a CV of ±20% for the d(v0,5), d(v0,9) and d(v0,99) are considered within the experimental error. In a preferred embodiment, the anti-muscarinic drug is glycopyrronium bromide, the ICS is beclometasone dipropionate, the LABA is formoterol fumarate dihydrate, and the salt of fatty acid is magnesium stearate.

Accordingly, in a particularly embodiment, the invention is directed to a powder formulation for use in any dry powder inhaler comprising:

(A) a carrier, comprising:

(a) a fraction of coarse particles of a physiologically acceptable carrier having a mean particle size of at least 175 μm; and (b) a fraction of fine particles consisting of a mixture of 90 to 99.5 percent by weight of particles of a physiologically acceptable excipient and 0.5 to 10 percent by weight of magnesium stearate, wherein at least 90% of all said fine particles have a volume diameter lower than 15 microns, wherein the weight ratio of said fine particles to said coarse particles is 5:95 to 30:70; and (B) micronized particles of glycopyrronium bromide, formoterol fumarate dihydrate, and, optionally, beclometasone dipropionate, as active ingredients, wherein said formulation is obtainable by a process comprising:

(i) mixing said carrier, said formoterol fumarate dihydrate, and, optionally, said beclometasone dipropionate in a vessel of a shaker mixer at a speed of rotation not lower than 16 r.p.m. for a time of not less than 60 minutes, to obtain a first mixture; and (ii) adding said glycopyrronium bromide to said first mixture, to obtain a second mixture, and mixing said second mixture at a speed of rotation not higher than 16 r.p.m. for a time of not more than 40 minutes; and whereby a mid-fine particle fraction of glycopyrronium bromide is higher than 25%, preferably from 28 to 40%.

Advantageously, in order to better achieve the distal tract of the respiratory tree, 90% of the micronized particles of beclometasone dipropionate (BDP) and formoterol fumarate dihydrate shall have a volume diameter lower than 6.0 micron, preferably equal to or lower than 5.0 micron, the volume median diameter shall be from 1. to 2.5 micron, preferably from 1.3 to 2.2 micron, and no more than 10% of said shall have a diameter lower than 0.6 micron, preferably equal to or lower than 0.7 micron, more preferably equal to or lower than 0.8 micron.

It follows that the width of the particle size distribution of the particles of the BDP and formoterol fumarate dihydrate, expressed as a span, shall be advantageously from 1.0 to 4.0, more advantageously from 1.2 to 3.5.

In the case of glycopyrronium bromide, in order to achieve both the distal and upper tract of the respiratory tree, 90% of the micronized particles shall have a volume diameter equal to or lower than 8.0 micron, preferably equal to or lower than 7.0 micron, the volume median diameter shall be from 1.2 to 4.0 micron, preferably from 1.7 to 3.5 micron, and no more than 10% of said have a diameter lower than 0.5 micron, preferably equal to or lower than 0.8 micron, more preferably equal to or lower than 1.0 micron.

It follows that the width of the particle size distribution of the particles of the anticholinergic drug, expressed as a span, shall be advantageously from 1.0 to 5.0, more advantageously from 1.2 to 4.0.

More advantageously, it would also be preferable that the micronized particles of BDP have a Specific Surface Area comprised of 5.5 to 7.0 $m^2/g$, preferably from 5.9 to 6.8 m/g, the micronized particles of formoterol fumarate dihydrate have a Specific Surface Area comprised of 5 to 7.5 $m^2/g$, preferably from 5.2 to 6.5 $m^2/g$, more preferably from 5.5 to 5.8 $m^2/g$, and the micronized particles of glycopyrronium bromide have a Specific Surface Area of 1.8 to 5.0 m/g, preferably from 2.0 to 4.5 $m^2/g$.

The Specific Surface Area is determined by Brunauer-Emmett-Teller (BET) nitrogen adsorption method according to a known procedure known.

All the micronized active ingredients utilized in the formulation according to the invention may be prepared by processing in a suitable mill according to known methods.

In one embodiment of the invention, they could be prepared by grinding using a conventional fluid energy mill such as commercially available jet mill micronizers having grinding chambers of different diameters.

Depending on the type of the apparatus and size of the batch, the person skilled in the art shall suitably adjust the milling parameters such as the operating pressure, the feeding rate and other operating conditions to achieve the desired particle size. Preferably all the micronized active ingredients are obtained without using any additive during the micronization process.

In an embodiment of the invention, the micronized particles of glycopyrronium bromide may be prepared according to the process disclosed in WO 2014/173987, which is incorporated herein by reference in its entirety.

The powder formulation comprising micronized particles of glycopyrronium bromide, beclometasone dipropionate, and formoterol fumarate dihydrate as active ingredients obtainable according to process of the present invention is physically and chemically stable, freely flowable and exhibits a good homogeneity of the active ingredients.

Moreover, the above powder formulation is able of delivering a high respirable fraction, as measured by the fine particle fraction (FPF), for all the three active ingredients.

In particular, said formulation gives rise to a FPF significantly higher than 50% for all the three active ingredients, with an extrafine FPF higher than 10% for beclometasone dipropionate, and formoterol fumarate dihydrate, and a mid FPF higher than 25%, preferably equal to or higher than 28%, more preferably comprised between 28 and 40% for glycopyrronium bromide.

The ratio between the carrier particles and the active ingredients will depend on the type of inhaler used and the required dose.

The powder formulations of the invention may be suitable for delivering a therapeutic amount of all active ingredients in one or more actuations (shots or puffs) of the inhaler.

Advantageously, the formulations of the invention shall be suitable for delivering a therapeutically effective dose of all three active ingredients of 50 to 600 μg, preferably from 100 to 500 μg.

For example, the formulation will be suitable for delivering 3-15 μofg formoterol (as fumarate dihydrate) per actuation, advantageously 4-13.5 μg per actuation; 25-240 μg of beclometasone dipropionate (BDP) per actuation, advantageously 40-220 μg per actuation; and 5-65 μg of glycopyrronium (as bromide) per actuation, advantageously 11-30 μg per actuation. n a particularly preferred embodiment of the invention, the formulation is suitable for delivering 3 or 6 μg or 12 μg of formoterol (as fumarate dihydrate) per actuation; 50 or 100 or 200 μg of beclometasone dipropionate per actuation; and 6.5 or 12.5 μg or 25 μg of glycopyrronium (as bromide) per actuation.

In a particular embodiment, the formulation is suitable for delivering 6 μg of formoterol (as fumarate dihydrate) per actuation, 100 μg of becometasone dipropionate, and 12.5 μg of glycopyrronium (as bromide) per actuation.

In another embodiment, the formulation is suitable for delivering 12 μg of formoterol (as fumarate dihydrate) per actuation, 200 μg of beclometasone dipropionate, and 25 μg of glycopyrronium (as bromide) per actuation.

The dry powder formulation of the invention may be utilized with any dry powder inhaler.

Dry powder inhaler (DPIs) can be divided into two basic types:
  i) single dose inhalers, for the administration of single subdivided doses of the active compound; each single dose is usually filled in a capsule; and
  ii) multidose inhalers pre-loaded with quantities of active principles sufficient for longer treatment cycles.

On the basis of the required inspiratory flow rates (l/min) which in turn are strictly depending on their design and mechanical features, DPI's are also divided in:
  i) low-resistance devices (>90 l/min);
  ii) medium-resistance devices (about 60-90 l/min);
  iii) medium-high resistance devices (about 50-60 l/min); and
  iv) high-resistance devices (less than 30 l/min).

The reported classification is generated with respect to the flow rates required to produce a pressure drop of 4 KPa (KiloPascal) in accordance with the European Pharmacopoeia (Eur Ph), which is incorporated herein by reference in its entirety.

The dry powder formulations of the invention are particularly suitable for multidose DPIs comprising a reservoir from which individual therapeutic dosages can be withdrawn on demand through actuation of the device, for example that described in WO 2004/012801, which is incorporated herein by reference in its entirety.

Other multidose devices that may be used are, for instance, Diskus™ of GlaxoSmithKline, Turbohaler™ of AstraZeneca Twisthaler™ of Schering, Clickhaler™ of Innovata, Spiromax™ of Teva, Novolizer™ of Meda, and Genuair™ of Almirall.

Examples of marketed single dose devices include Rotohaler™ of GlaxoSmithKline, Handihaler™ of Boehringer Ingelheim, and Breezehaler™ of Novartis.

Preferably, the formulation according to the invention is utilized with the DPI device sold under the trademark of NEXThaler™ and disclosed in WO 2004/012801, which is incorporated herein by reference in its entirety, or its variants disclosed in the application no. PCT/EP2015/063803, which is incorporated herein by reference in its entirety, being particularly suitable for the delivery of extrafine formulations.

To protect the DPIs from ingress of moisture into the formulation, it may be desirable to overwrap the device in a flexible package capable of resisting moisture ingress such as that disclosed in EP 1 760 008, which is incorporated herein by reference in its entirety.

Administration of the formulation prepared according to the process of the invention is indicated for the prevention and/or treatment of chronic obstructive pulmonary disease (COPD) and asthma of all types and severity.

The formulation prepared according to the process of the invention is also indicated for the prevention and/or treatment of further respiratory disorders characterized by obstruction of the peripheral airways as a result of inflammation and presence of mucus such as chronic obstructive bronchiolitis.

In certain embodiments, said formulation is particularly suitable for the prevention and/or treatment of severe and/or very severe forms COPD, and in particular for the maintenance treatment of COPD patients with symptoms, airflow limitation and history of exacerbations.

Furthermore, it might be suitable for the prevention and/or treatment of persistent asthma and asthma in patients not controlled with medium or high doses of ICS in combination with LABAs.

Other features of the invention will become apparent in the course of the following descriptions of exemplary embodiments which are given for illustration of the invention and are not intended to be limiting thereof.

EXAMPLES

Example 1. Preparation of the Carrier

Micronized alpha-lactose monohydrate (DFE Pharma, Germany) having the following particle size was used: $d(v0.1)=1.7$ micron; $d(v0.5)=4.3$ micron: and $d(v0.9)=9.8$ micron.

About 3388 g of said micronized alpha-lactose monohydrate mixed with about 69.17 g of magnesium stearate (Peter Greven, Germany) were fed into the vessel of a dyna-MIX™ mixer (Willy A. Bachofen AG, Germany) and mixed with fissured coarse particles of α-lactose monohydrate having a mass diameter of 212-355 micron in the ratio 10:90 percent by weight. The mixing was carried out for 240 minutes at a speed of rotation of 16 and 24 r.p.m. alternatively for the two rotation axes.

The ratio between micronized alpha-lactose monohydrate and magnesium stearate is 98:2 percent by weight.

The resulting mixture of particles is termed hereinafter the "carrier.

The extent to which the magnesium stearate (MgSt) coats the surface of the fine and coarse lactose particles was determined by water contact angle measurement, and then by applying the equation known in the literature as Cassie and Baxter according to the conditions reported in the specification. The surface coating turned out to be of 26%.

Example 2. Preparation of the Dry Powder Formulation

Micronized formoterol fumarate dihydrate having the following particle size was used: $d(v0.1)=0.9$ micron; $d(v0.5)=2.3$ micron; and $d(v0.9)=4.2$ micron.

Beclometasone dipropionate (BDP) having the following particle size was used: $d(v0.1)=0.7$ micron; $d(v0.5)=1.5$ micron; and $d(v0.9)=2.8$ micron.

Glycopyrronium bromide (GB) having the following particle size was used: $d(v0.1)=0.39$ micron; $d(v0.5)=1.91$ micron; $d(v0.9)=4.77$ micron.

The carrier as obtained in Example 1 was mixed in a dyna-MIX™ mixer with formoterol fumarate dihydrate and BDP at a speed of rotation between 22 and 28 r.p.m. for the two rotation axes for a time of 88 minutes.

Then glycopyrronium bromide was added and mixed at a speed of rotation between 15 and 13 r.p.m. alternatively for the two rotation axes for a time of 36 minutes.

The resulting mixture was poured into a sieving machine available from Frewitt (Fribourg, Switzerland) equipped with a 600 micron mesh size sieve.

Upon sieving, the blend was finally mixed in a in the dyna-MIX™ mixer for 60 minutes of 15 and 13 r.p.m. alternatively for the two rotation axes, to achieve an homogeneous distribution of the active ingredients.

The ratio of the active ingredients to 10 mg of the carrier is 6 microgram (μg) of FF dihydrate (theoretical delivered dose 4.5 μg), 100 microgram (μg) of BDP and 12.5 microgram (μg) of glycopyrronium bromide (theoretical delivered dose 10.0 μg).

The powder formulation was characterized in terms of the uniformity of distribution of the active ingredients and aerosol performances after loading it in the multidose dry powder inhaler described in WO 2004/012801, which is incorporated herein by reference in its entirety.

The uniformity of distribution of the active ingredients was evaluated by withdrawing 12 samples from different parts of the blend and evaluated by HPLC.

The results (mean value±RSD) are reported in Table 1.

The evaluation of the aerosol performance was carried out using the Next Generation Impactor (NGI) according to the conditions reported in the European Pharmacopeia 8.5 Ed 2015, par 2.9.18, pages 309-320, which is incorporated herein by reference in its entirety. After aerosolization of 3 doses from the inhaler device, the NGI apparatus was disassembled and the amounts of drug deposited in the stages were recovered by washing with a solvent mixture and then quantified by High-Performance Liquid Chromatography (HPLC)

The following parameters, were calculated: i) the delivered dose which is the amount of drug delivered from the device recovered in the all parts of impactor; ii) the fine particle mass (FPM) which is the amount of delivered dose having a particle size equal to or lower than 5.0 micron; iii) the extrafine FPM which is the amount of delivered dose having a particle size equal to or lower than 2.0 micron and/or equal to or lower than 1.0 micron and; iv) the mid FPM which is the amount of delivered dose having a particle size comprised between 2.0 and 5.0 micron; v) the fine particle fraction (FPF) which is the ratio between the fine particle mass and the delivered dose; and vi) the MMAD. The results (mean value±S.D) are reported in Table 1.

TABLE 1

| | Active ingredient |
| --- | --- |
| | FF |
| Uniformity of distribution | 99.4 (±1.4) |
| Delivered Dose [μg] | 5.99 (±0.3) |
| Fine Particle Mass [μg] | 4.14 |
| Fine Particle Fraction [%] | 69.4 |
| Mid Fine Particle Mass [μg] | 1.46 |
| Extrafine Particle Mass <2 μm [μg] | 2.67 |
| Extrafine Particle Mass <1 μm [μg] | 1.19 |
| Mid Fine particle Fraction [%] | 24.4 |
| Extrafine Particle Fraction <2 μm [%] | 44.6 |
| Extrafine Particle Fraction <1 μm [%] | 19.9 |
| MMAD [μm] | 1.65 |
| | GB |
| Uniformity of distribution | 100.8 (±1.6) |
| Delivered Dose [pg] | 11.66 (±0.4) |
| Fine Particle Mass [μg] | 7.85 |
| Fine Particle Fraction [%] | 67.2 |
| Mid Fine Particle Mass [μg] | 3.46 |
| Extrafine Particle Mass <2 μm [μg] | 4.39 |
| Extrafine Particle Mass <1 μm [μg] | 1.8 |
| Mid Fine particle Fraction [%] | 29.6 |
| Extrafine Particle Fraction <2 μm [%] | 37.6 |
| Extrafine Particle Fraction <1 μm [%] | 15.4 |

TABLE 1-continued

| | Active ingredient |
| --- | --- |
| MMAD [μm] | 1.92 |
| | BDP |
| Uniformity of distribution | 101.8 (±1.1) |
| Delivered Dose [μg] | 97.4 (±3.2) |
| Fine Particle Mass [μg] | 67.6 |
| Fine Particle Fraction [%] | 69.4 |
| Mid Fine Particle Mass [μg] | 17.6 |
| Extrafine Particle Mass <2 μm [μg] | 50 |
| Extrafine Particle Mass <1 μm [μg] | 27.9 |
| Mid Fine particle Fraction [%] | 18 |
| Extrafine Particle Fraction <2 μm [%] | 51.4 |
| Extrafine Particle Fraction <1 μm [%] | 28.7 |
| MMAD [μm] | 1.25 |

From the data of Table 1, it can be appreciated that the powder formulation show both an excellent homogeneity, and a high respirable fraction (FPF), for all the three active ingredients.

On the other hand, as for glycopyrrolate is concerned, a higher mid FPF is obtained than those achieved with the formulations disclosed Table 3 of WO 2015/004243 (about 30% vs about 20%).

Analogous performances could be obtained if different active ingredients belonging to the class of ICS, LABAs and anticholinergics are utilized provided that they have a very similar particle size.

Example 3. Preparation of the Dry Powder Formulation

The powder formulation was prepared as described in Example 2, but the ratio of the active ingredients to 10 mg of the carrier is 6 microgram (μg) of FF dihydrate (theoretical delivered dose 4.5 μg), 100 microgram (μg) of BDP and 25 microgram (μg) of glycopyrronium bromide (theoretical delivered dose 20.0 μg).

The uniformity of distribution of the active ingredients and the aerosol performances were evaluated as reported in Example 2. The results are reported in Table 2.

TABLE 2

| | Active ingredient |
| --- | --- |
| | FF |
| Uniformity of distribution | 99.6 (±1.6) |
| Delivered Dose [μg] | 4.76 (±0.2) |
| Fine Particle Mass [μg] | 3.05 |
| Fine Particle Fraction [%] | 66.3 |
| Mid Fine Particle Mass [μg] | 1.05 |
| Extrafine Particle Mass <2 μm [μg] | 2.10 |
| Extrafine Particle Mass <1 μm [g] | 0.78 |
| Mid Fine particle Fraction [%] | 22.0 |
| Extrafine Particle Fraction <2 μm [%] | 44.1 |
| Extrafine Particle Fraction <1 μm [%] | 16.3 |
| MMAD [μm] | 1.63 |
| | GB |
| Uniformity of distribution | 101.5 (±2.5) |
| Delivered Dose [μg] | 20.03 (±0.8) |
| Fine Particle Mass [μg] | 11.43 |
| Fine Particle Fraction [%] | 57.1 |
| Mid Fine Particle Mass [μg] | 5.94 |
| Extrafine Particle Mass <2 μm [μg] | 5.49 |
| Extrafine Particle Mass <1 μm [μg] | 1.75 |
| Mid Fine particle Fraction [%] | 29.7 |
| Extrafine Particle Fraction <2 μm [%] | 27.4 |
| Extrafine Particle Fraction <1 μm [%] | 8.7 |

TABLE 2-continued

| | Active ingredient |
|---|---|
| MMAD [μm] | 2.15 |
| BDP | |
| Uniformity of distribution | 100.2 (±1.2) |
| Delivered Dose [μg] | 80.9 (±3.1) |
| Fine Particle Mass [μg] | 50.0 (±1.2) |
| Fine Particle Fraction [%] | 61.8 |
| Mid Fine Particle Mass [μg] | 17.3 |
| Extrafine Particle Mass <2 μm [μg] | 32.7 |
| Extrafine Particle Mass <1 μm [μg] | 13.1 |
| Mid Fine particle Fraction [%] | 21.4 |
| Extrafine Particle Fraction <2 μm [%] | 40.3 |
| Extrafine Particle Fraction <1 μm [%] | 16.2 |
| MMAD [μm] | 1.62 |

From the data of Table 2, it can be appreciated that the powder formulation shows both an excellent homogeneity, and a high respirable fraction (FPF), for all the three active ingredients.

As far as glycopyrrolate is concerned, a-mid FPF of about 30% is obtained.

Reference Example from WO 2015/004243

Two powder formulations according to the teaching of Example 1, 3, 4 and 5 of WO 2015/004243, which is incorporated herein by reference in its entirety, were prepared. Their aerosol performances, evaluated as reported in Example 2 of the present application, are reported in Table 4. MF is for mechano-fusion apparatus and CY is for Cyclomix™ apparatus.

TABLE 3

| | Batch CY | Batch MF |
|---|---|---|
| FF | | |
| Delivered Dose [μg] | 5.3 | 5.8 |
| Fine Particle Mass [μg] | 4.0 | 4.3 |
| Fine Particle Fraction [%] | 75.9 | 73.4 |
| Extrafine Particle Mass Fraction <2 μm [μg] | 3.0 | 3.2 |
| Mid Fine Particle Mass [μg] | 1.00 | 1.07 |
| Extrafine Fine Particle Fraction <2 μm [%] | 56.6 | 55.2 |
| Mid Fine Particle Fraction [%] | 18.8 | 18.4 |
| MMAD [μm] | 1.16 | 1.16 |
| GB | | |
| Delivered Dose [μg] | 11.6 | 11.9 |
| Fine Particle Mass [μg] | 6.6 | 6.4 |
| Fine Particle Fraction [%] | 53.8 | 57.2 |
| Extrafine Particle Mass <2 μm [μg] | 4.0 | 4.0 |
| Mid Fine Particle Mass [μg] | 2.6 | 2.5 |
| Extrafine Particle Fraction <2 μm [%] | 34.5 | 33.6 |
| Mid Fine Particle Fraction [%] | 22.4 | 21.0 |
| MMAD [μm] | 1.78 | 1.75 |
| BDP | | |
| Delivered Dose [μg] | 90.6 | 95.7 |
| Fine Particle Mass [μg] | 64.5 | 66.9 |
| Fine Particle Fraction [%] | 71.2 | 69.9 |
| Extrafine Particle Mass <2 μm [μg] | 48.8 | 50.0 |
| Mid Fine Particle Mass [μg] | 15.7 | 16.9 |
| Extrafine Particle Fraction <2 μm [%] | 53.9 | 52.2 |
| Mid Fine Particle Fraction [%] | 17.3 | 17.7 |
| MMAD [μm] | 1.08 | 1.13 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing a powder formulation for inhalation for use in a dry powder inhaler, said powder formulation comprising:
    (A) a carrier, comprising:
        (a) a fraction of coarse particles of a physiologically acceptable carrier having a mean particle size of at least 175 μm; and
        (b) a fraction of fine particles, comprising a mixture of 90 to 99.5 percent by weight of particles of a physiologically acceptable excipient and 0.5 to 10 percent by weight of a salt of a fatty acid, wherein at least 90% of all said fine particles having a volume diameter lower than 15 microns,
        wherein the weight ratio of said fine particles to said coarse particles 5:95 to 30:70; and
    (B) micronized particles of an antimuscarinic drug, a long-acting $\beta_2$-agonist, and, optionally, an inhaled corticosteroid, as active ingredients, wherein said antimuscarinic drug comprises glycopyrronium bromide, and said long-acting $\beta_2$-agonist comprises formoterol fumarate dihydrate,
    wherein said process comprises:
        (i) mixing said carrier, said long-acting $\beta_2$-agonist, and, optionally, said inhaled corticosteroid in a vessel of a shaker mixer at a speed of rotation not lower than 16 rpm for a time of not less than 60 minutes, to obtain a first mixture; and
        (ii) adding said anti-muscarinic drug to said first mixture, to obtain a second mixture, and mixing said second mixture at a speed of rotation not higher than 16 rpm for a time of not more than 40 minutes, to obtain said formulation,
    wherein the mid-fine particle fraction of glycopyrronium bromide is higher than 25%.

2. A process according to claim 1, further comprising:
    (iii) further mixing said formulation obtained in (ii), to achieve a homogeneous distribution of said active ingredients.

3. The process according to claim 1, wherein said long-acting $\beta_2$-agonist further comprises at least one selected from the group consisting of formoterol, salmeterol, indacaterol, olodaterol, and vilanterol.

4. The process according to claim 1, wherein said antimuscarinic drug further comprises at least one selected from the group consisting of glycopyrronium chloride, tiotropium bromide, umeclidinium bromide, and aclidinium bromide.

5. The process according to claim 1, wherein said inhaled corticosteroid is selected from the group consisting of beclomethasone dipropionate and its monohydrate form, budesonide, fluticasone propionate, fluticasone furoate, and mometasone furoate.

6. The process according to claim 1, wherein said inhaled corticosteroid is beclometasone dipropionate.

7. The process according to claim 1, wherein said salt of a fatty acid is selected from the group consisting of magnesium stearate, sodium stearyl fumarate, sodium stearyl lactylate, sodium lauryl sulfate, and magnesium lauryl sulfate.

8. The process according to claim 7, wherein said salt of the fatty acid is magnesium stearate.

9. A powder formulation for use in any dry powder inhaler, comprising:
(A) a carrier, comprising:
(a) a fraction of coarse particles of a physiologically acceptable carrier having a mean particle size of at least 175 μm; and
(b) a fraction of fine particles comprising a mixture of 90 to 99.5 percent by weight of particles of a physiologically acceptable excipient and 0.5 to 10 percent by weight of magnesium stearate, wherein at least 90% of all said fine particles have a volume diameter lower than 15 microns,
wherein the weight ratio of said fine particles to said coarse particles is 5:95 to 30:70; and
(B) micronized particles of glycopyrronium bromide, formoterol fumarate dihydrate, and, optionally, beclometasone dipropionate, as active ingredients,
wherein said formulation is obtainable by a process comprising:
(i) mixing said carrier, said formoterol fumarate dihydrate, and, optionally, said beclometasone dipropionate in a vessel of a shaker mixer at a speed of rotation not lower than 16 rpm for a time of not less than 60 minutes, to obtain a first mixture; and
(ii) adding said glycopyrronium bromide to said first mixture, to obtain a second mixture, and mixing said second mixture at a speed of rotation not higher than 16 rpm for a time of not more than 40 minutes, to obtain said formulation; and
wherein the mid-fine particle fraction of glycopyrronium bromide is higher than 25%.

10. The powder according to claim 9, wherein said process further comprises:
(iii) further mixing said formulation obtained in (ii), to achieve a homogeneous distribution of said active ingredients.

11. The powder formulation according to claim 9, wherein said mid-fine particle fraction is from 28 to 40%.

12. The powder formulation according to claim 9, wherein said physiologically acceptable excipient is alpha-lactose monohydrate.

13. The powder formulation according to claim 9, wherein the coarse particles have a mass diameter of 210 to 360 μm.

14. A dry powder inhaler device, containing a dry powder formulation according to claim 9.

15. A method for the treatment of an inflammatory and/or obstructive airways disease, comprising administering to a subject in need thereof an effective amount of a dry powder formulation according to claim 9.

16. The method of claim 15, wherein said disease is asthma or chronic obstructive pulmonary disease (COPD).

* * * * *